US006840959B2

United States Patent
Treacy et al.

(10) Patent No.: US 6,840,959 B2
(45) Date of Patent: Jan. 11, 2005

(54) PELVIC PROSTHESIS PLUS METHODS AND TOOLS FOR IMPLANTATION

(75) Inventors: Patrick J. Treacy, Kinnelon, NJ (US); Damon Servidio, Montville, NJ (US); Lawrence R. Menendez, Marina Del Rey, CA (US); Kathleen N. Burns, Edgewater, NJ (US)

(73) Assignee: Howmedica Ostenics Corp., Mahwah, NJ (US)

(*) Notice: Subject to any disclaimer, the term of this patent is extended or adjusted under 35 U.S.C. 154(b) by 104 days.

(21) Appl. No.: 09/899,448

(22) Filed: Jul. 5, 2001

(65) Prior Publication Data

US 2003/0009234 A1 Jan. 9, 2003

(51) Int. Cl.[7] ................................................. A61F 2/34
(52) U.S. Cl. ............................. 623/22.22; 623/22.32; 623/22.35; 623/22.38
(58) Field of Search .......................... 623/22.12, 22.22, 623/23.43, 22.15, 22.21, 22.24, 22.32, 22.35, 22.36, 22.38, 22.43; A61F 2/32, 2/34, 2/36

(56) References Cited

U.S. PATENT DOCUMENTS

| | | |
|---|---|---|
| 3,641,590 A | 2/1972 | Michele |
| 3,698,017 A | 10/1972 | Scales et al. |
| 3,740,769 A | 6/1973 | Haboush |
| 3,744,061 A | 7/1973 | Frost |
| 3,896,504 A | 7/1975 | Fischer |
| 3,918,102 A | 11/1975 | Joachim |
| 4,092,741 A | 6/1978 | David |
| 4,245,360 A | 1/1981 | Brinckmann et al. |
| 4,645,507 A | 2/1987 | Engelbrecht et al. |
| 4,743,262 A | 5/1988 | Tronzo |
| 5,030,238 A | 7/1991 | Nieder et al. |
| 5,176,711 A | 1/1993 | Grimes |
| 5,326,367 A | 7/1994 | Robioneck |
| 5,609,646 A | 3/1997 | Field et al. |
| 5,702,477 A | 12/1997 | Capello et al. |
| 5,871,548 A | 2/1999 | Sanders et al. |
| 5,888,207 A | 3/1999 | Nieder et al. |
| 5,931,870 A * | 8/1999 | Cuckler et al. ............... 623/16 |
| 6,162,257 A * | 12/2000 | Gustilo et al. ........... 623/22.32 |
| 6,416,553 B1 * | 7/2002 | White et al. ............. 623/22.38 |
| 6,458,161 B1 * | 10/2002 | Gibbs et al. ............. 623/22.32 |
| 6,620,200 B1 * | 9/2003 | Descamps et al. ....... 623/22.32 |

FOREIGN PATENT DOCUMENTS

| | | | | |
|---|---|---|---|---|
| DE | 39 03 438 A1 | * | 8/1990 | .......... A61F/02/32 |
| FR | 2651995 A1 | * | 3/1991 | .......... A61F/02/34 |
| FR | 2 689 000 A1 | * | 10/1993 | ............. A61F/2/34 |
| FR | 2819172 A1 | * | 7/2002 | .......... A61F/02/34 |
| JP | 2031750 | * | 2/1990 | ............. A61F/2/28 |
| JP | 5023363 | * | 2/1993 | .......... A61F/02/34 |
| RU | 2117460 | * | 8/1998 | .......... A61F/02/32 |

OTHER PUBLICATIONS

Waldmer Link GMBH & Co Saddle Prosthesis, publication.
Stryker Howmedica Osteonics "Restoration Gap II Revision Acetabular System", publication.
The Pelvice Endoprosthesis–An Alternative To Hemi–Pelvectomy In The Case Of Tumer Patients; Z. Othop: Jan. 2, 1974 p. 968–970.

* cited by examiner

Primary Examiner—David H. Willse
Assistant Examiner—Javiel G. Blanco
(74) Attorney, Agent, or Firm—Lerner, David, Littenberg, Krumholz & Mentlik, LLP

(57) ABSTRACT

A pelvic prosthesis includes a ball socket and two substantially parallel fanned wings extending upward from the socket. A stabilizing hump is located directly above the socket and extends between and substantially perpendicular to the fanned wings. Each wing is provided with at least two pin receiving holes such that pins may be inserted through the fanned wing. The holes are preferably arranged so that the pins, when inserted, are not parallel. The anterior fanned wing is approximately twice as tall as the posterior fanned wing. Methods and tools for implanting the prosthesis are also disclosed.

7 Claims, 8 Drawing Sheets

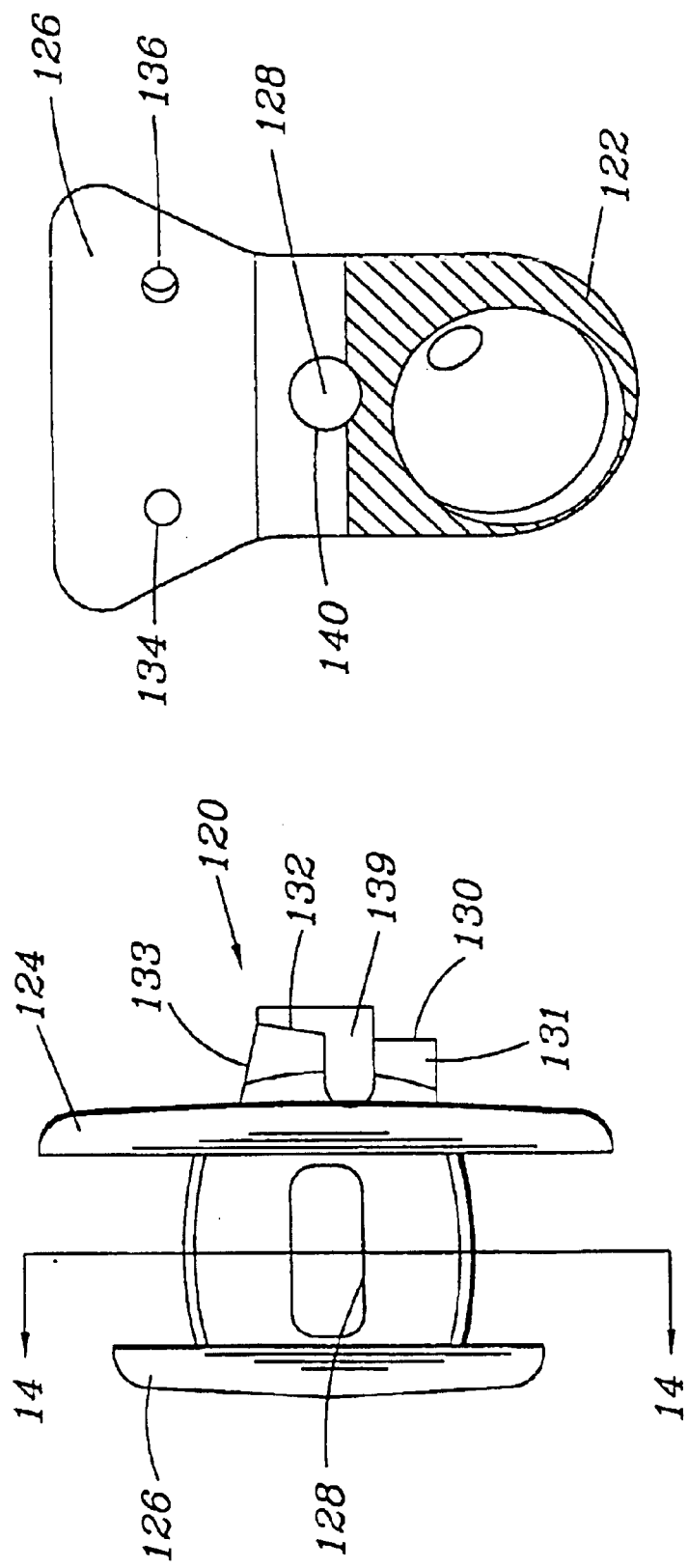

PELVIC PROSTHESIS PLUS METHODS AND TOOLS FOR IMPLANTATION

BACKGROUND OF THE INVENTION

1. Field of the Invention

The invention relates to implantable prostheses. More particularly, the invention relates to an implantable pelvic prosthesis including an acetabular component, as well as tools and methods for implanting the prosthesis. The prosthesis is used for reconstruction of the hip and hip joint after resection of the pelvis. It provides a stable link between the femur and the pelvis without resorting to an excision arthroplasty.

2. Brief Description of the Prior Art

The hip joint is a ball-and-socket type joint in which the ball-shaped femoral head is engaged with and articulates with a cup-shaped socket known as the acetabulum. Injury and/or disease may damage the hip joint (and/or indeed the pelvis itself) to the extent that the joint, portions of the pelvis and/or combinations thereof must be replaced by or be augmented with a prosthetic device.

Furthermore, deterioration of the acetabulum itself, and particularly the cartilage within the acetabulum, requires that a prosthetic acetabular shell be mounted within a prepared area of the acetabulum. The acetabular shell receives and articulates with a prosthetic femoral head which is installed on a proximal portion of a patient's femur.

In some instances, degenerative bone conditions deteriorate the acetabulum, and particularly its medial wall, to the extent that the acetabulum does not have the integrity to serve as a mounting platform for a prosthetic acetabular shell. Thus, the acetabular component of the prosthesis must be designed to securely attach to whatever bone mass is available. Such mass may be severely limited in instances, for example, where the pelvis is ravaged by cancer. There have been many different proposed designs for an acetabular component and pelvic prostheses suitable for use in the above described situations. The following examples serve to illustrate the state of the art.

U.S. Pat. No. 4,245,360 discloses a partial pelvic prosthesis having an implant piece corresponding to that part of the pelvis to be resected, the piece having a receiving space for the acetabular fossa and connecting bores, and a recess for connecting prosthetic elements whereby the elements can produce the required connection between the implant piece and the pelvis.

The invention disclosed in the '360 patent has threaded bores to receive screws for adjustably fixing prosthetic elements in bores and recess. It is a disadvantage of this device that it chews up bone stock. This actually exacerbates the condition sought to be overcome and greatly complicates revision surgery (replacement of a failed or worn prosthetic component).

U.S. Pat. No. 4,645,507 discloses a prosthesis which has a shaft which carries a bearing at one end. The bearing has a rim at its junction with the shaft. The end of the bearing opposite the rim has a saddle-shaped portion including a pair of protrusions which flank a depression. The depression has a pair of bearing surfaces separated by a protuberance which is formed in the depression and extends from one of the protrusions to the other.

According to the teachings of the '507 patent, the prosthesis is installed at a hip joint by inserting the shaft into the end of the femur nearest the pelvis. The shaft is pushed into the femur until the rim on the bearing contacts the end of the femur. One of the protrusions is passed through an opening in the wall of the pelvis so that the wall is received in the depression of the bearing.

The wall is contoured so as to conform to the shape of the depression and the protuberance therein and rests on the surface of the protuberance as well as the bearing surfaces of the depression. When the prosthesis has been installed in this manner, relative pivotal movement of the femur and the pelvis is possible.

The prosthesis described in the '507 patent makes it possible to obtain relative pivotal movement of the femur and the pelvis even when the pelvis has been damaged or has deteriorated to such an extent that the natural socket can neither be repaired nor replaced. However, the implant is unstable and easily dislocates.

U.S. Pat. No. 5,030,238 discloses a hip prosthesis wherein a saddle-shaped head has a seat flanked by two horns and engageable with the surface bounding a recess in the lower part of a damaged pelvic bone. The head is rotatably or rigidly secured to a substantially S-shaped adapter which, in turn, is rotatably or non-rotatably secured to the adjacent end of a shank that is implantable in the cavity of a femur. One or more distancing rings can be inserted between the adapter and the head.

The device described in the '238 patent was intended to overcome the shortcomings of the device described in the '507 patent.

In particular, as stated in the '238 patent:

" . . . heretofore known prostheses with saddle-like heads fail to satisfy all of the requirements which must be fulfilled by an artificial hip joint.

First of all, when the wearer of the prosthesis is walking, relative movement between the head of the prosthesis and the socket of the pelvis entails a pronounced mechanical stressing of the remainder of the pelvis. When the pelvis and the femur perform large movements relative to each other, the horns of the saddle-like head of the implanted prosthesis strike the adjacent portions of the pelvis.

Secondly, frictional engagement between the head of the implanted prosthesis and the adjacent portion of the pelvis brings about extensive wear upon the pelvis; in fact, the head is likely to penetrate into the pelvis and to shorten the respective lower extremity of the patient."

Furthermore, according to the 238' patent:

"It was further discovered that, when the pelvis has undergone extensive damage (either as a result of an accident or as a result of illness), the muscles in the region of an implanted conventional prosthesis with a saddle-like head can exert only relatively small forces in a sense to straighten out the extremity into which the prosthesis is implanted because they are incapable of finding an appropriate lever arm for the application of conversion or transmission forces which are being generated thereby. Therefore, a patient wearing such a prosthesis is likely to limp because she or he must continuously strive to maintain the center of gravity of the body above the vertical axis which is common to the saddle-like head and the shank of the implanted artificial hip joint."

Despite the recognition of many of the disadvantages of the prior saddle-like prostheses, the solution proposed by the '238 patent is not ideal. It requires the use of many pins. This results in bone loss which complicates revision surgery. In addition, the prosthesis of the '238 patent provides only limited movement.

U.S. Pat. No. 5,326,367 discloses an endoprosthesis for cancer damaged hip bones which has a recess in a distal portion to receive a prosthetic hip socket.

The endoprosthesis described in the '367 patent includes an individual distal part and an individual proximal part which are secured to each other by means of a screw connection. The distal and the proximal part include mounting brackets for screwing the parts to the hip bone or, respectively, to a vertebra. In addition, the proximal and distal parts are shaped to positively inter-engage each other. This device overcomes the problems inherent in the saddle-like prostheses but requires the use of a number of screws to affix it to the hip bone.

U.S. Pat. No. 5,871,548 discloses a modular acetabular reinforcement system having a substantially cup-shaped reinforcement body with a peripheral flange portion. One or more fixation wings, of various sizes and shapes, are selectively and separately attachable to the flange portion of the reinforcement body.

The system disclosed in the '548 patent is mountable within the acetabulum of a patient to reinforce the acetabulum and to serve as a platform for other prosthesis components such as an acetabular shell. This device is similar to the device described in the '367 patent insofar as it is not a saddle-like prosthesis and it is affixed to the bone with many screws. It is an advantage that the "wings" may be affixed to extend radially from almost any location on the peripheral flange. The disadvantage is that it requires the use of a number of screws to affix it to the hip bone.

SUMMARY OF THE INVENTION

It is therefore an object of the invention to provide a pelvic prosthesis.

It is also an object of the invention to provide a pelvic prosthesis which is suitable for use where the patient has suffered considerable bone loss due to either injury or illness such as cancer.

It is another object of the invention to provide a pelvic prosthesis which does not have the disadvantages of the prior art saddle-like components.

It is yet another object of the invention to provide a pelvic prosthesis which does not require extensive bone damage during implant.

It is another object of the invention to provide a pelvic prosthesis which does not require the use of a substantial number of screws for implantation.

It is still another object of the invention to provide methods and tools for implanting the pelvic prosthesis.

In accord with these objects which will be discussed in detail below, an pelvic prosthesis according to the invention includes a ball socket adapted to replace the acetabulum and two substantially parallel fanned wings extending upward from the ball socket. A stabilizing hump is located directly above the ball socket and extends between and substantially perpendicular to the fanned wings.

According to the presently preferred embodiment, each fanned wing is provided with at least two pin receiving holes such that the pins may be inserted through one fanned wing (for example, the anterior fanned wing), into the other fanned wing. The holes are preferably arranged so that the pins, when inserted, are not parallel. Further according to the presently preferred embodiment, the anterior fanned wing is approximately twice as tall as the posterior fanned wing.

Methods for implanting the pelvic prosthesis of the invention utilize a trial component which is substantially similar to the prosthetic component but includes some additional features. The holes on the anterior fanned wing of a preferred embodiment of the trial component have collars and act as drill guides. An alternative embodiment of the invention contemplates utilization of simple through holes as drill guides. A semicircular trough is formed where the stabilizing hump would be by a notch preparation drill guide which is provided in the fanned wings substantially coaxial with the semicircular hump.

According to the presently preferred embodiment, the anterior fanned wing is also provided with a pair of windows on either side of the aforementioned notch preparation drill guide.

The methods for implanting the pelvic prosthesis include resecting the pelvis as needed to make room for the implant, placing the trial component over the ilium, aligning the trial component with the aid of the windows, drilling holes in the ilium using the drill guides, installing temporary pins in the holes, notching the bottom of the bone using the third hole as a guide, removing the temporary pins and the trial component, placing the implant over the ilium, aligning the holes in the fanned wings with the holes drilled in the ilium and aligning the hump with the notch, inserting pins through the holes, adding cement between the fanned wings and the bone, and inserting a liner in the ball socket prior to inserting the ball of a femoral component.

According to the invention, the fanned wings distribute stresses over a larger area. The two pins are not used for fixation. The pins are used for alignment and support while grout is added and they reinforce the cured grout.

The use of grout works well in a compression situation and prevents dislocation. The non-parallel relationship of the pins allows easier insertion and a smaller incision. The notch and hump engagement provides better implant stability.

Since the trial component has a ball socket substantially the same as the implant, the practitioner can attach the femoral component to the trial component to inspect the alignment of the trial component before finally determining the location of the implant. The ball socket in the implant (and the trial component) accommodates a variety of liners, for example constrained and/or non-constrained liners.

The invention further contemplates the possible use of femoral extension devices. The length and shape of a given femoral extension device is variable and would be designed to connect the ball (inserted into the pelvic prosthesis), of the ball and socket, with a femoral component. Those skilled in the art will readily appreciate that the use of an extension device is indicated in, for example, situations where it is necessary to correct for leg length and/or offset.

Additionally, those skilled in the art will readily appreciate that the prosthesis contemplated by the invention could be used in conjunction with prostheses implanted when performing typical hip replacement (femoral head and stem); segmented replacement and/or total femur replacements.

BRIEF DESCRIPTION OF THE DRAWINGS

FIG. 13 is a top view of the trial component;

FIG. 14 is a section taken along line 14—14 of FIG. 13;

DETAILED DESCRIPTION

Figure 1:
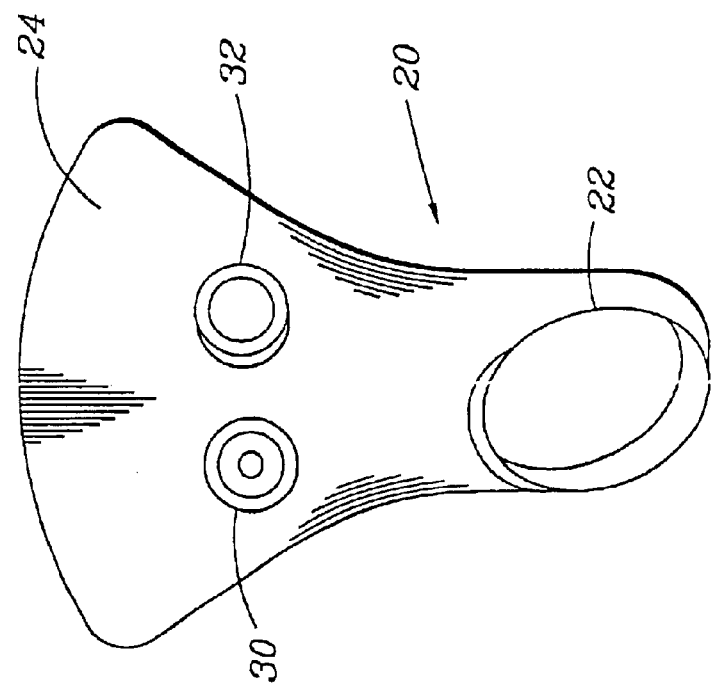
FIG. 1 is a perspective view of a pelvic prosthesis according to the invention.
Figure 2:
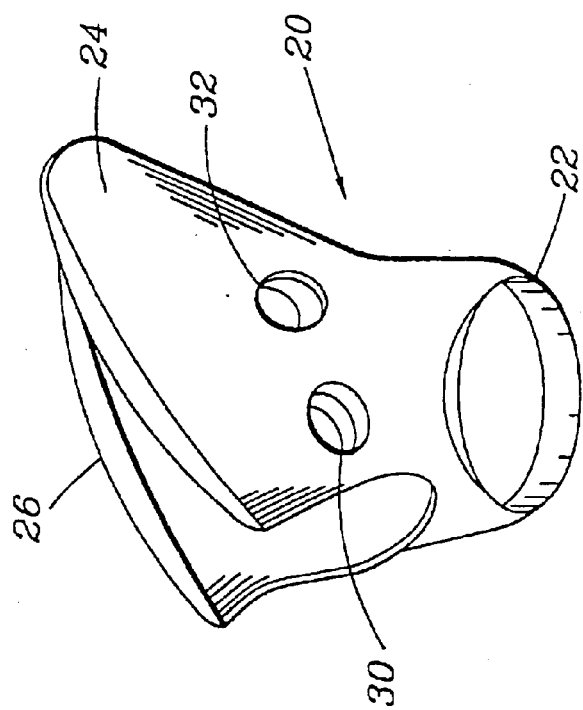
FIG. 2 is an anterior plan view of the prosthesis.
Figure 4:
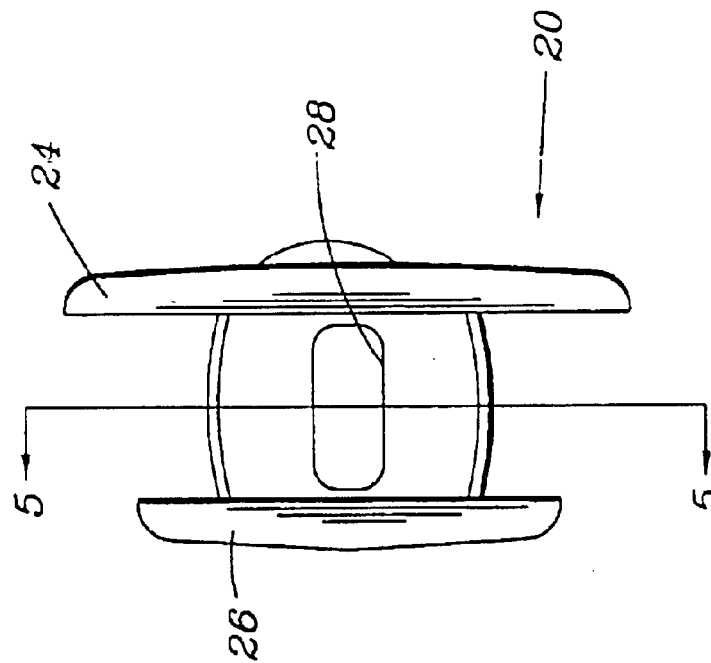
FIG. 4 is a top view of the prosthesis.

Turning now to FIGS. 1 through 7, a pelvic prosthesis 20 according to the invention includes a ball socket 22 adapted to replace the acetabulum and two substantially parallel fanned wings 24, 26 extending upward from the ball socket 22. A stabilizing hump 28 is located directly above the ball socket 22 and extends between and substantially perpendicular to the fanned wings 24, 26.

According to the presently preferred embodiment, the anterior fanned wing 24 is provided with at least two pin receiving holes, for example a lateral side hole 30 and a medial side hole 32. The posterior fanned wing 26 is provided with corresponding pin receiving holes 34, 36.

Figure 7:
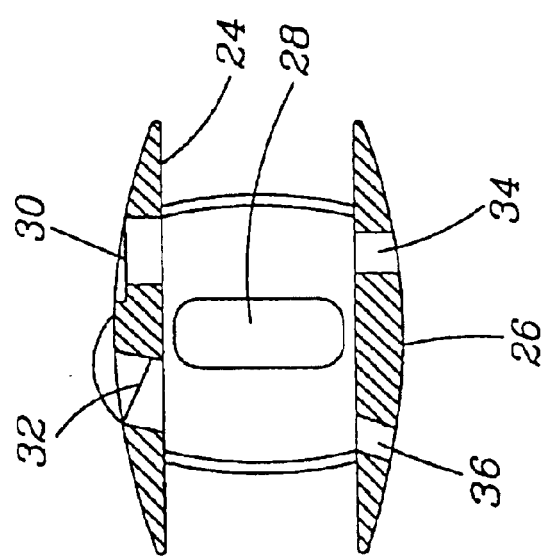
FIG. 7 is a section taken along line 7—7 in FIG. 6.

As seen best in FIG. 7, the holes 30, 32 in the anterior fanned wing 24 have countersinks for receiving the heads of pins. Also as seen best, in FIG. 7, the holes are aligned such that the pins may be inserted through the anterior fanned wing into the posterior fanned wing. The holes are preferably arranged so that the pins, when inserted, are not parallel.

As is further shown in FIG. 7, the lateral side holes 30 and 34 are aligned so that a pin extending through them is substantially parallel to the hump 28. The medial side holes 32 and 36 are aligned so that a pin extending through them extends at an angle to the hump 28. More particularly, the pin is angled from lateral to medial.

Figure 3:
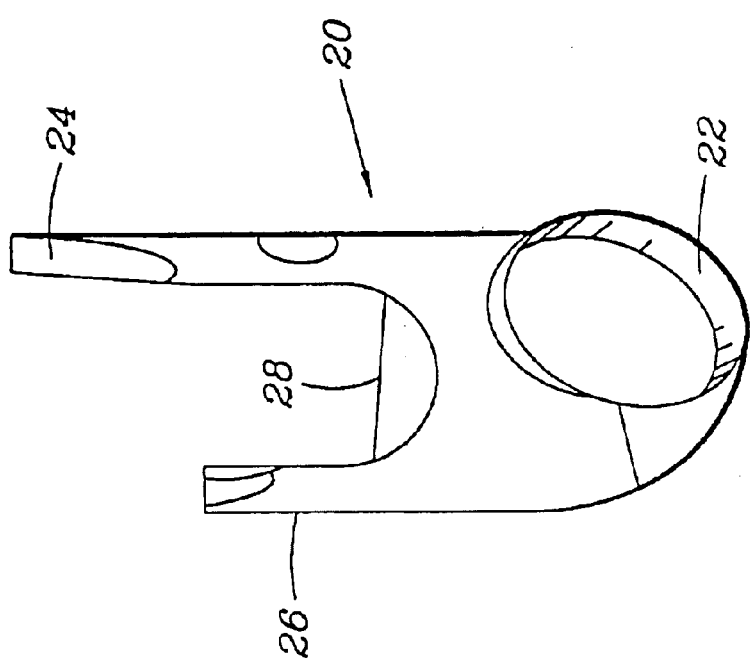
FIG. 3 is a side view of the prosthesis.
Figure 6:
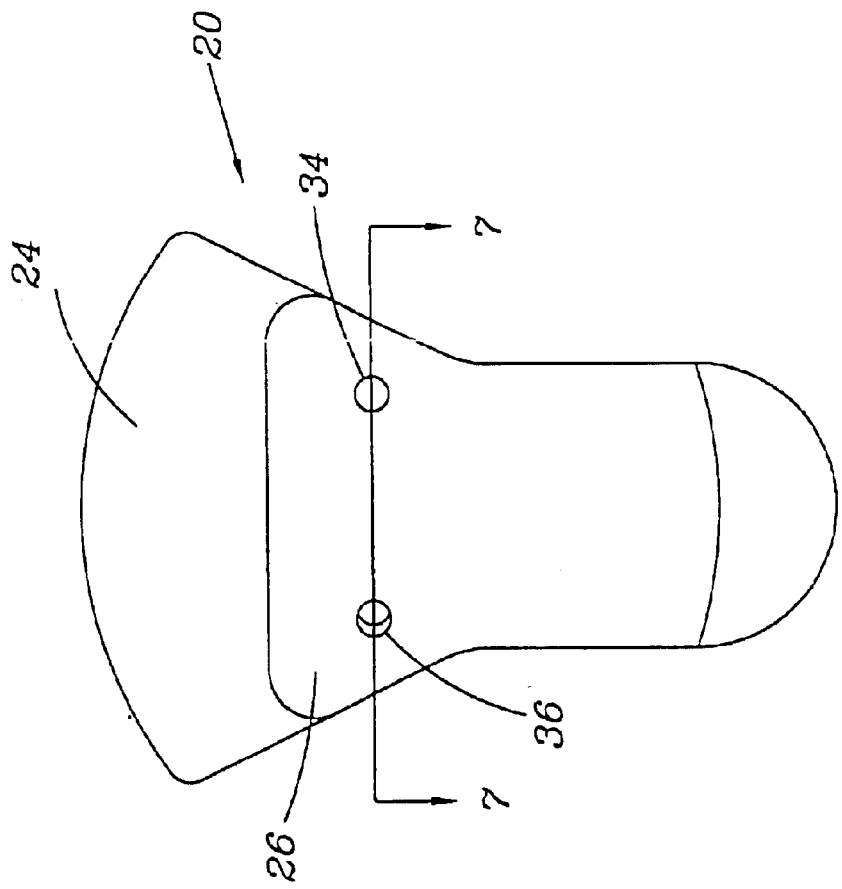
FIG. 6 is a posterior plan view of the prosthesis.
Figure 5:
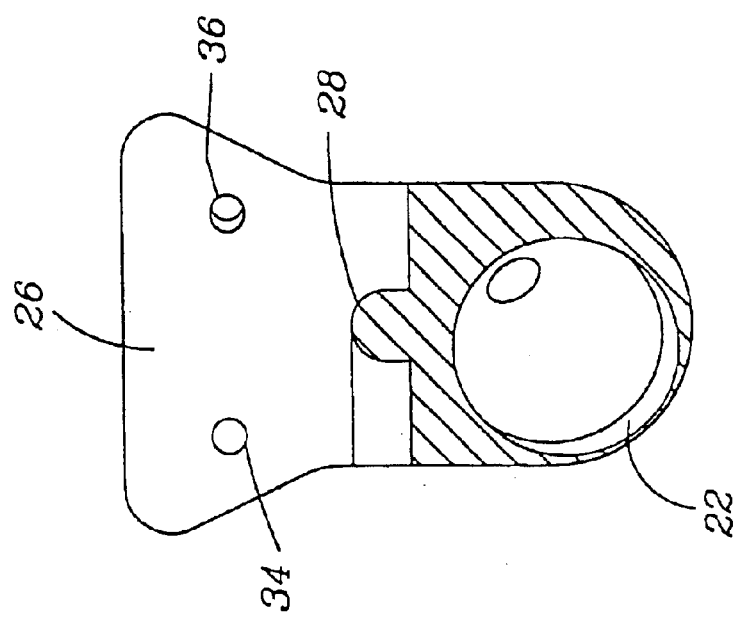
FIG. 5 is a section taken along line 5—5 in FIG. 4.
Figure 8:
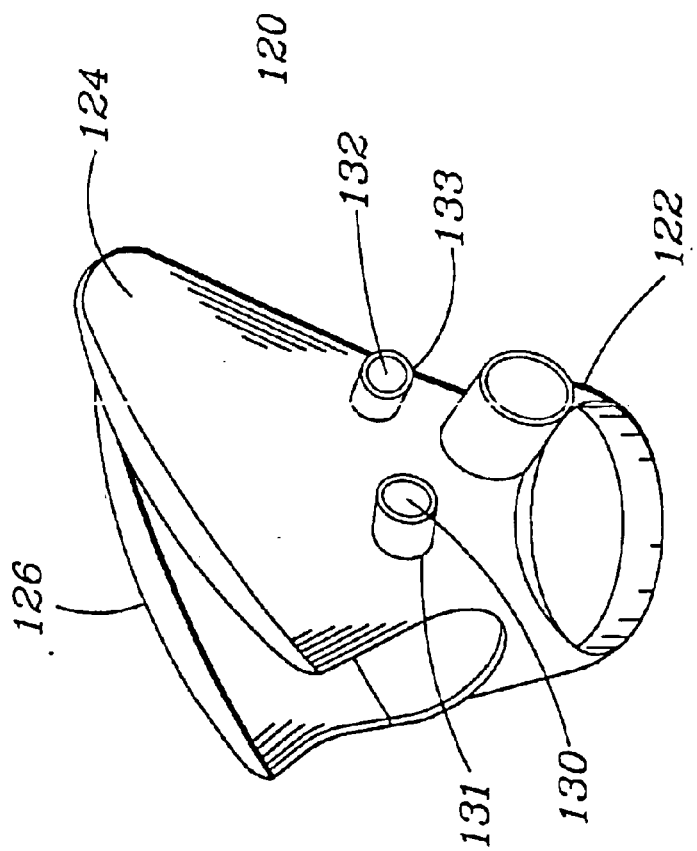
FIG. 8 is a perspective view of a trial component according to the invention.

Further according to the presently preferred embodiment, and as seen best in FIGS. 3 and 6, the anterior fanned wing 24 is approximately twice as tall as the posterior fanned wing 26.

Methods for implanting the pelvic prosthesis of the invention utilize a trial component which is substantially similar to the prosthetic component but includes some additional features.

Referring now to FIGS. 8–14 a trial component 120 according to the invention includes a ball socket 122 and two substantially parallel fanned wings 124, 126 extending upward from the ball socket 122. The anterior fanned wing 124 is provided with at least two pin receiving holes, for example a lateral side hole 130 and a medial side hole 132. The posterior fanned wing 126 is provided with corresponding pin receiving holes 134, 136.

Figure 10:
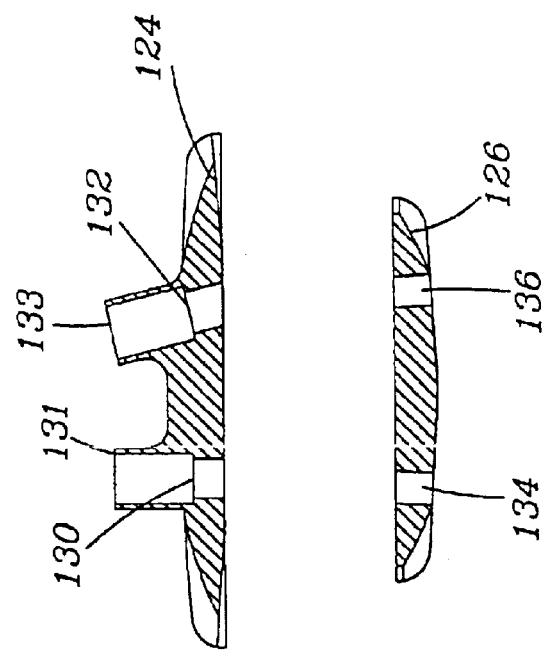
FIG. 10 is a section taken along line 10—10 in FIG. 9.

As seen best in FIG. 10, the holes are aligned such that two pins may be inserted through the anterior fanned wing into the posterior fanned wing. The holes are preferably arranged so that the pins, when inserted, are not parallel.

As is further shown in FIG. 10, the lateral side holes 130 and 134 are aligned so that a pin extending through them is substantially orthogonal to the fanned wings. The medial side holes 132 and 136 are aligned so that a pin extending through them extends at an angle. More particularly, the pin is angled from lateral to medial.

The two holes 130, 132 on the anterior fanned wing 124 of the trial component 120 have collars 131, 133 and act as drill guides. As seen best in FIG. 14, a semicircular trough 128 is located where the stabilizing hump would be in the implant.

Figure 11:
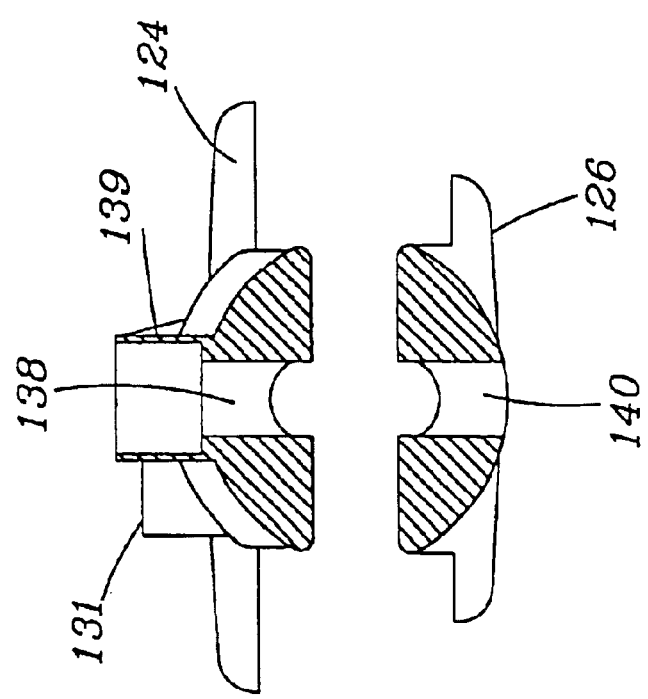
FIG. 11 is a section taken along line 11—11 in FIG. 9.

As seen best in FIG. 11, notch preparation drill guide 138 is provided in the anterior fanned wing 124 and a corresponding notch preparation drill guide 140 is provided in the posterior fanned wing 126, to facilitate preparation of a notch corresponding to stabilizing hump 28 on prosthesis 20.

As seen best in FIGS. 11 and 14, drill guides 138, 140 are substantially coaxial with the semicircular trough 128. A drill guide collar 139 is provided adjacent to drill guide 138.

Figure 9:
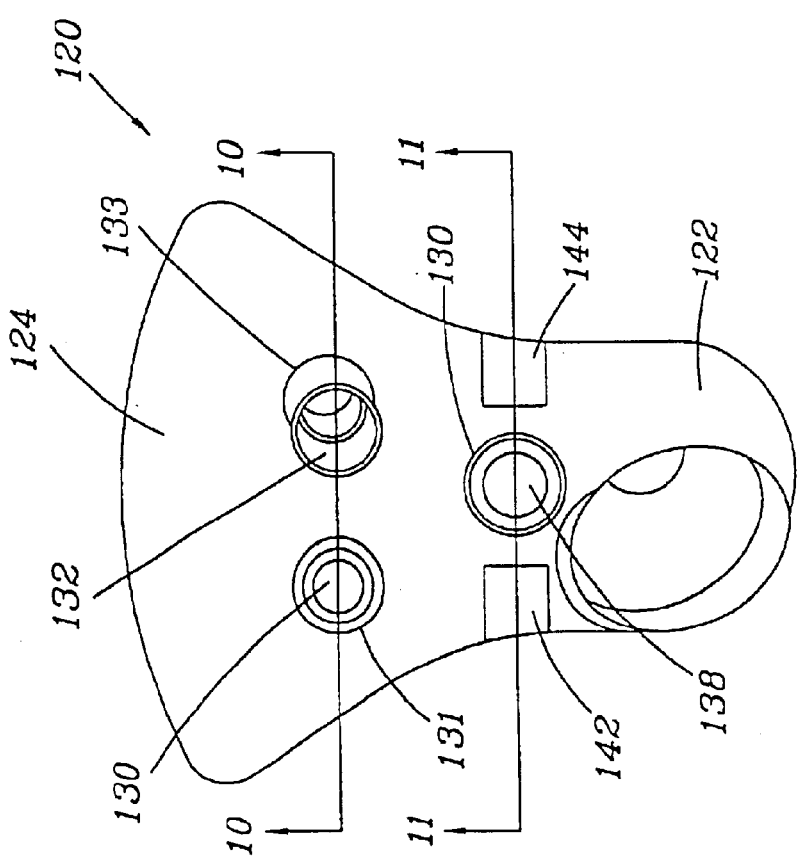
FIG. 9 is an anterior plan view of the trial component.
Figure 12:
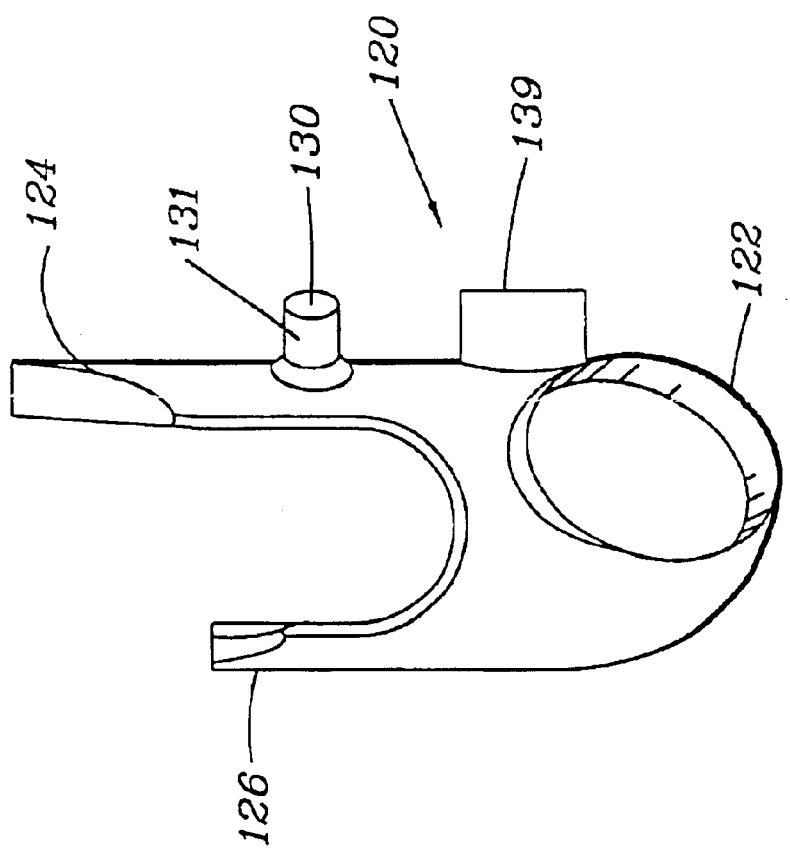
FIG. 12 is a side view of the trial component.

As seen best in FIG. 9, according to the presently preferred embodiment, the anterior fanned wing 124 is also provided with a pair of windows 142, 144 on either side of the third hole 138.

The methods for implanting the pelvic prosthesis 20 include resecting the pelvis as needed to make room for the implant 20, placing the trial component 120 over the ilium aligning the component 120 with the aid of the windows 142, 144, drilling at least two holes in the ilium using the drill guides 130, 132, installing temporary pins (not shown) in the holes, notching the bottom of the bone using drill guide 138, removing the temporary pins and the trial component.

After the trial component is removed the bone has at least two pin holes and a notch.

The methods continue with placing the implant 20 over the ilium, aligning the holes in the fanned wings with the holes drilled in the ilium and aligning the hump with the notch, inserting pins through the holes, adding cement between the fanned wings and the bone, and inserting a liner in the ball socket prior to inserting the ball of a femoral component.

As mentioned above, according to the invention, the fanned wings distribute stresses over a larger area. The pins are not used for fixation. The pins are used for alignment and support while grout is added and they reinforce the cured grout. The use of grout works well in a compression situation and prevents dislocation. The non-parallel relationship of the pins allows easier insertion and a smaller incision. The notch and hump engagement provides better implant stability.

Since the trial component has a ball socket substantially the same as the implant, the practitioner can attach the femoral component to the trial component to inspect the alignment of the trial component before finally determining the location of the implant. The ball socket in the implant (and the trial component) accommodates either a constrained or non-constrained liner.

From the foregoing, those skilled in the art will appreciate that separate left and right implants and trial components are necessary.

As previously indicated the invention further contemplates the possible use of femoral extension devices. The length and shape of a given femoral extension device is variable and would be designed to connect the ball (inserted into the pelvic prosthesis), of the ball and socket, with a femoral component. Those skilled in the art will readily appreciate that the use of an extension device is indicated in, for example, situations where it is necessary to correct for leg length and/or offset.

Figure 15:
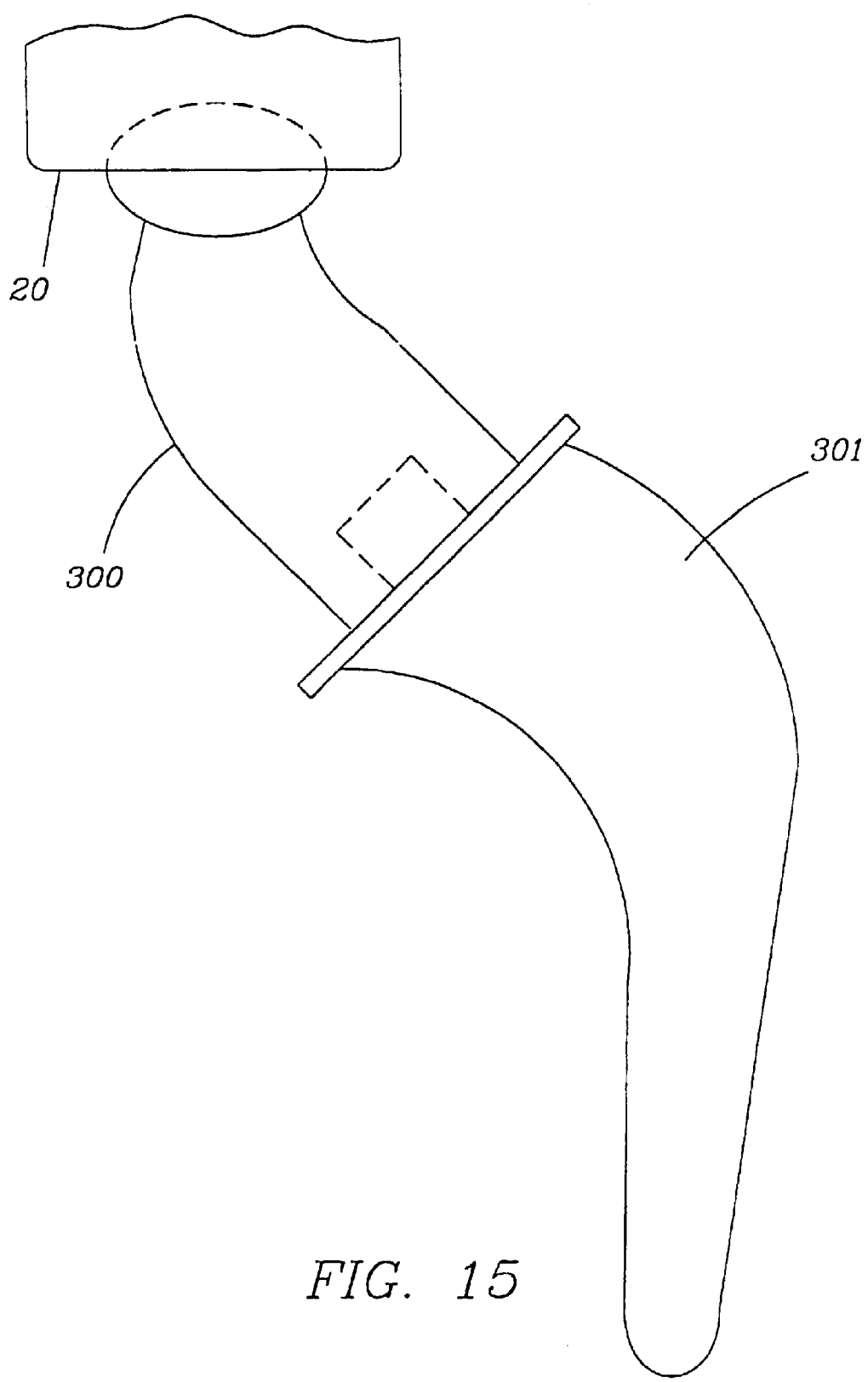
FIG. 15 depicts an exemplary femoral extension device contemplated by the invention.

Reference should be made to FIG. 15 which depicts an exemplary femoral extension device contemplated by the invention.

In particular, FIG. 15 shows a femoral extension device 300 of the type used to used to interconnect exemplary femoral component 301 to the previously described socket in pelvic prosthesis 20. The femoral extension device shown in FIG. 15 is meant to be illustrative only, with those skilled in the art being able to readily appreciate that such devices may be designed in a variety of lengths and shapes.

There have been described and illustrated herein a pelvic prosthesis and tools and methods for implanting the component. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

What is claimed is:

1. A pelvic prosthesis comprising:

a ball socket adapted to replace the acetabulum;

an anterior fanned wing extending upward from said ball socket; and a posterior fanned wing extending upward from said ball socket, said posterior fanned wing being spaced apart from said anterior fanned wing;

wherein said anterior fanned wing defines at least two spaced apart pin receiving holes;

said posterior fanned wing defines two spaced apart pin receiving holes which are aligned with said pin receiving holes defined by said anterior fanned wing;

said spaced apart holes on said anterior fanned wing include a lateral anterior hole and a medial anterior hole, and said spaced apart holes on said posterior fanned wing include a lateral posterior hole and a medial posterior hole hold; and said lateral anterior hole, said medial anterior hole, said lateral posterior hole, and said medial posterior hole are arranged such that a first pin extending through said lateral anterior hole and said lateral posterior hole is not parallel to a second pin extending through said medial anterior hole and said medial posterior hole.

2. The pelvic prosthesis of claim 1 wherein said posterior fanned wing is substantially parallel to said anterior fanned wing.

3. The pelvic prosthesis of claim 1 wherein said ball socket utilizes a constrained liner.

4. The pelvic prosthesis of claim 1 wherein said fanned wings are offset curved surfaces.

5. The pelvic prosthesis of claim 1 further comprising a stabilizing hump extending between and substantially perpendicular to said anterior fanned wing and said posterior fanned wing.

6. The pelvic prosthesis of claim 1 further comprising an extension device for interconnecting the pelvic prosthesis with a femoral component.

7. The pelvic prosthesis of claim 1 wherein said anterior fanned wing is substantially taller than said posterior fanned wing.

* * * * *

UNITED STATES PATENT AND TRADEMARK OFFICE
CERTIFICATE OF CORRECTION

PATENT NO. : 6,840,959 B2
DATED : January 11, 2005
INVENTOR(S) : Patrick J. Treacy et al.

It is certified that error appears in the above-identified patent and that said Letters Patent is hereby corrected as shown below:

Title page,
Item [73], Assignee, "Ostenics" should read -- Osteonics --.

Column 1,
Line 52, after "in", insert -- the --.

Column 7,
Line 2, cancel the second occurrence of "used to".
Lines 28 and 30, "spaced apart" should read -- spaced-apart --.

Column 8,
Lines 1 and 3, "spaced apart" should read -- spaced-apart --.
Line 5, cancel "hold".

Signed and Sealed this

Nineteenth Day of April, 2005

JON W. DUDAS
*Director of the United States Patent and Trademark Office*